United States Patent

Schuldink

[11] Patent Number: 5,997,296
[45] Date of Patent: Dec. 7, 1999

[54] EXPLORATORY DEVICE WITH POTTING MATERIAL

[75] Inventor: Hendrikus Egbert Schuldink, Nieuwleusen, Netherlands

[73] Assignee: Jonkers Data B.V., Nieuwleusen, Netherlands

[21] Appl. No.: 09/094,050

[22] Filed: Jun. 9, 1998

[51] Int. Cl.⁶ .................................................. A61C 19/04
[52] U.S. Cl. ............................................. 433/72; 433/115
[58] Field of Search ................................ 433/72, 75, 114, 433/115, 116, 229

[56] References Cited

U.S. PATENT DOCUMENTS

| 3,943,914 | 3/1976 | Greenfell et al. | 433/72 X |
| 4,995,403 | 2/1991 | Beckman et al. | 433/72 X |
| 5,022,856 | 6/1991 | Zimble | 433/72 |
| 5,354,200 | 10/1994 | Klein et al. | 433/72 |

FOREIGN PATENT DOCUMENTS

| 94 18 713 U | 4/1995 | Germany . |
| 94 18 844 U | 4/1995 | Germany . |
| 295 00 933 U | 5/1995 | Germany . |
| 94 19 769 U | 6/1995 | Germany . |
| 44 38 603 C2 | 4/1998 | Germany . |
| 44 41 441 C2 | 4/1998 | Germany . |

*Primary Examiner*—Nicholas D. Lucchesi
*Attorney, Agent, or Firm*—Lahive & Cockfield, LLP

[57] ABSTRACT

In a device with an elongate housing for examining the gums of a patient, with the housing having a connecting area for connecting a replaceable, movable exploratory tip and with mechanical and/or electronic detection elements provided in the housing for detecting and converting the movements of the exploratory tip. The invention proposes that the detection elements be designed to be liquid-tight and/or liquid-resistant, and surrounded by a potting compound inside the housing.

16 Claims, 1 Drawing Sheet

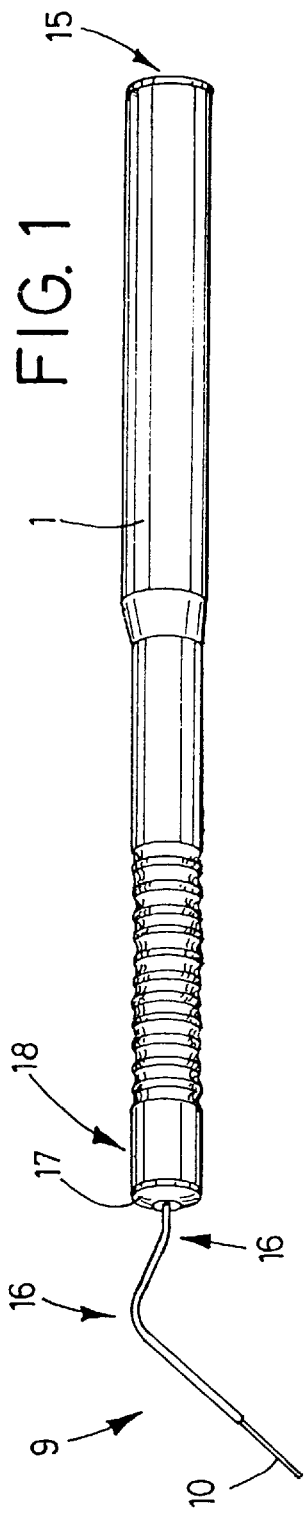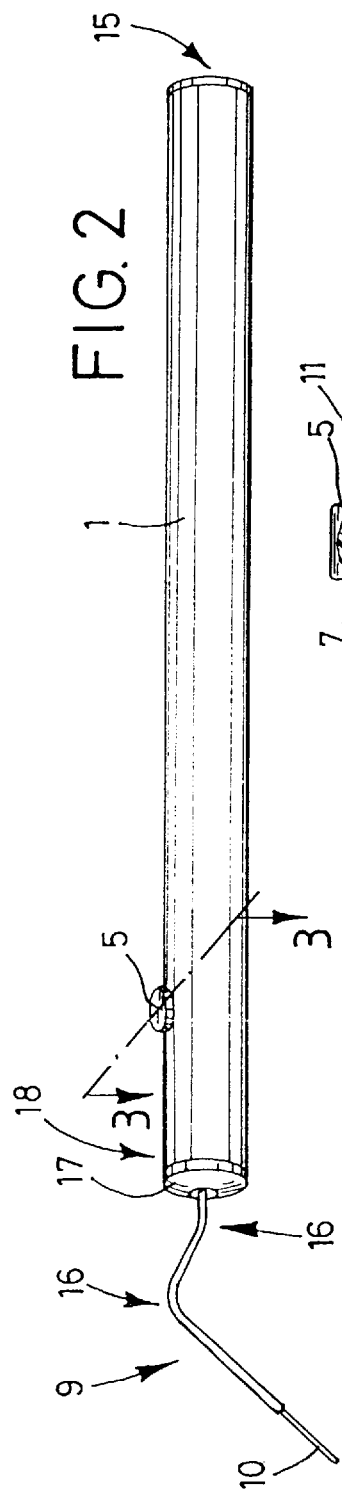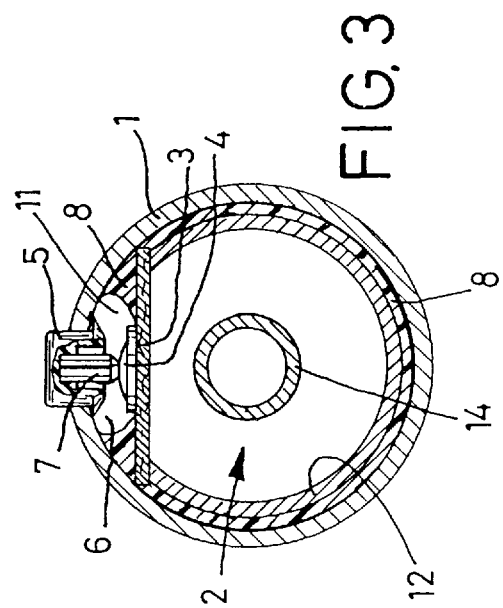

EXPLORATORY DEVICE WITH POTTING MATERIAL

BACKGROUND OF THE INVENTION

The invention relates to an exploratory device for examining the oral cavity of a person. Devices of this kind are known in the art and described for example in DE 44 38 603 A1.

Prior art exploratory devices general comprise an elongate housing having a connecting area for connecting a releasable movable exploratory tip. The housing includes a mechanical or electronic element for detecting and converting movements of the exploratory tip into usable signals. These prior art devices are generally constructed such that the electronics located inside the housing RE temperature-resistant, so that the entire exploratory device can be sterilized at temperatures of for example 134° C. to 156° C.

An object of the present invention is to provide an improved exploratory device that is relatively easy to handle, relatively sturdy and relatively safe to operate.

SUMMARY OF THE INVENTION

The present invention provides an exploratory device that employs a potting material that is configured to cover the detection or conversion circuit or element(s) located in a housing of the device. For this purpose, the detection structure is either designed to be liquid-resistant, for example electronic components that can be surrounded directly by the potting compound, or is designed to be liquid-tight, for example a small tube that receives a spring and into which a mechanical transmission rod can extend that transmits the movement of the exploratory tip.

By potting the electronic or mechanical assemblies (e.g., the detection structure) provided in the housing, they are effectively protected against entry of the sterilizing atmosphere so that adverse effects on the mechanical or electrical components during sterilization can be reliably prevented. In addition, the potting compound further provides improved mechanical stability against blows or impacts or the like on the housing, such as those that occur if the device inadvertently falls to the floor.

Another advantage of employing the potting compound is that it allows the device to be sterilized directly without further protective measures, and therefore does not have to be sterilized in a special sheath for example, so that the handling of the device is facilitated and simplified. In addition, the potting compound forms a protective jacket about the detection components to protect them against contamination, thus making the device more robust and less prone to damage.

Provision can be made for initially potting the above-mentioned components and then inserting the entire unit into the housing. This unit can then be provided with elastic outer projections that permit insertion into the housing against a certain resistance. The projections thus provide a shock-absorbent mounting of the unit inside the housing. Further provision can be made for the potting compound to extend up to the inside wall of the housing.

Alternatively, provision can be made for potting the housing components in the housing itself, i.e. after they have been inserted into the housing, with the remaining space being filled by a potting compound, so that the potting compound extends up to the inside wall of the housing and forms a connection with it as by gluing. Thus, gaps and spaces within the housing can be filled with the potting compound, thus eliminating potential contamination sites, which are undesirable despite the apparent ability to sterilize them with known techniques.

The potting compound can advantageously consist of two components so that reliable curing of the potting compound can be ensured even without air being admitted inside the housing. Very thin compounds are advantageously used for this purpose, so that remaining air inclusions can be eliminated and the space between the detection means located in the housing and the housing itself can be filled reliably and completely.

The exploratory device according to the invention has one or more buttons by which the evaluation and storage electronics can be controlled. According to the invention, the buttons are advantageously provided with replaceable button caps that extend through the housing. The replaceability of the button caps makes it possible to remove the button caps at certain intervals and to clean thoroughly the cavities located beneath the button caps.

Advantageously the button cap can have a barbed projection, for example, in the shape of a circumferential edge that tapers conically, to facilitate insertion of the button cap into an opening in the housing. When the button cap is subsequently removed from the housing, deliberate damage to the button cap projection is caused thereto by the shape of the housing, so that button caps, once removed, cannot be reused. In this fashion, a seal that is as dirt-tight or contamination-proof as possible can be provided between the button cap and the housing, and new button caps can be installed exclusively in the housing.

An insertion device for installing the button cap can be provided in the form of a small tube that tapers conically, into which tube the button cap is inserted at the top, with the small tube extending into the opening in the housing. The button cap is then inserted into the small tube using a pusher, compressing the button cap and reducing its diameter so that the lower barbed projection on the button cap can be brought into a vacant space in the housing where it then expands again. The mounting tube can then be removed from the housing. Depending on the material properties of the button cap, provision can be made for allowing the newly installed button cap to be left alone for approximately 12 to 24 hours so that it can expand once more and slowly resume its original shape so that permanent seating of the button cap inside the housing is guaranteed.

The button cap can be advantageously made hollow so that it is easier to deform when it is inserted into the housing opening in the manner described above. In its interior it can accept a plunger made of an elastomer material, for example in the shape of a rubber rod, with this plunger serving to transmit the pressure to the probe provided inside the housing. The probe can be made using SMD technology, so that even when a sterilizing atmosphere penetrates the housing along the circumference of the button cap, the components located inside the housing remain functional. Because of the small structural dimensions of the probe, the plunger ensures functionally reliable operation of the probe when pressure is exerted on the button cap, since the rubber rod is located centrally in the button cap and hence centrally above the probe. Pressure on an area sufficient for reliable triggering of the probe can then be reinforced by the fact that the plunger tapers conically at its lower end adjacent the probe.

The potting compound and the avoidance of closed cavities inside the housing also advantageously ensure that partial areas of the device do not burst under sterilization conditions, as might otherwise be the case if there were air inclusions. A cavity that is free of potting compound and allows access to the probe for its operation is provided above the probe.

Alternatively, other operating possibilities can be used to keep the housing free of button knobs or similar actuating elements. Thus, an especially slender rod-like housing can be created that allows especially good access to the back teeth of a patient, so that the handling process is more comfortable for the patient and the aperture angle of the mouth required under these conditions can be kept smaller. For example, adjacent the exploratory tip, the housing of such a device that does not have a button can have an external diameter of only 8 mm over a length of 5 to 10 cm.

In a known design of similar dental instruments, provision can be made for the wire- or rod-shaped area of the exploratory tip to have two bends provided at a distance from one another, with the bends being in opposite directions, so that the overall result is not a J- or L-shaped bend but one that is approximately Z- or S-shaped and is provided in the portion of the exploratory tip that is in the form of a wire or small tube. In this way, additional assurance is provided that an examination behind the teeth of the patient can be performed without difficulty by being suitable for use with aperture angles of the mouth that are as small as possible.

The data acquired by the electronic or mechanical components can thus be stored advantageously with computer support, with the corresponding evaluation and storage electronics being provided in simple fashion in a so-called "organizer," such as a personal digital assistant (PDA) approximately the size of a hand, computer, or other processor. Such organizers are usually provided with interfaces that provide simple wired or wireless data transmission to larger computer systems. In addition, such PDA organizers accommodate the CPU of the computer, the keyboard, and a screen in a comparatively tiny space, so that this very compact unit can be covered in simple fashion by a transparent film and protected against contamination caused for example by spray from the patient's mouth. In view of the compact dimensions of such an organizer, this hygienic protection can be provided much more simply than if a computer with a modular design were employed, in which the CPU, keyboard, and screen constitute three separate assemblies connected with one another by cables.

In addition, a PDA organizer has the advantage of ease of transportability, so that a doctor can always have the organizer with him in various treatment rooms and can avoid the cost-intensive use of a different computer in each individual treatment room. This mobility also allows data acquisition outside the doctor's treatment rooms, for example when the doctor visits patients confined to bed at home or in a hospital.

BRIEF DESCRIPTION OF THE DRAWINGS

Embodiments of the invention will now be described in greater detail with reference to the following drawings.

FIG. 1 is a perspective view of a first device;

FIG. 2 is a perspective view similar to FIG. 1, but of a second device; and

FIG. 3 is a section along line 3—3 through the device in FIG. 2.

DESCRIPTION OF ILLUSTRATED EMBODIMENT

FIGS. 1 through 3 illustrate a housing 1 that is generally approximately tubular or cylindrical in shape, and which can have changing diameters, FIG. 1, or even be composed slightly convex, conical, or with a polygonal cross-section. The elongate slender shape of the housing 1 facilitates handling of the device during use.

As illustrated in FIG. 3, the housing 1 mounts acquisition structure 2 for acquiring and possibly transmitting movement of an exploratory tip 9 with a movable sensor point 10, which is connected to the housing 1 by a plug 17. The plug 17 is inserted into the housing 1 at a forward connection end and held therein by an elastomeric O-ring. The acquisition structure 2 can comprise appropriate electrical circuitry or selected mechanical components suitable for detecting movement of the tip 9 and for generating appropriate signals in response thereto. The anterior end area of the housing 1 that receives the plug 17 is referred to as the connecting area 18 for the exploratory tip 9.

The illustrated acquisition structure 2 can comprise, according to one practice, a tube 12 in which an inner tube 14 is provided. Suitable signal transmitting components extend from the sensor pin 10 into the inner tube 14. Sensors (not shown) can be provided between the tube 12 and the inner tube 14, so as to detect movement of the transmission means, either magnetically or by induction for example. The sensors determine the position of the sensor pin 10 as measured values in this fashion.

Thus for example the depth of pockets in the gums of a patient can be determined. The measured values can be fed through a transmission cable to a computer and evaluated and/or stored therein. The transmission cable can be connected to a plug provided at a rear end 15 of the housing 1.

The illustrated housing 1 can be free of externally projecting actuating elements, FIG. 1, and can have a maximum outside diameter of about 1 cm adjacent the connecting area 18 over a length of at least about 5 cm.

The acquisition structure 2 in the device shown in FIGS. 2 and 3 comprise a printed circuit board (PCB) 3 and a probe 4 located on the PCB 3 and designed using SMD technology, with a push-button 4 outside housing 1 being actuated by means of a button cap 5. In FIG. 2, only one such probe is provided. purely as an example. Probe 4 can serve to store the measured value detected at the moment by the exploratory tip 9. Additional functions and probes can be provided. Button cap 5 can be composed of TEFLON and can have a circumferential projection 6 at its lower end. The projection 6 can be shaped approximately as a barb, with a diagonal surface and a straight section.

Button cap 5 can be introduced into the matching opening in the housing 1 with the aid of the sloping surface of the projection, while the straight portion of the projection 6 holds the button cap 5 permanently inside the housing 1. Forceps can be used to remove button cap 5 from housing 1, destroying or damaging the projection 6 in the process, so that the interior of the housing 1 can be cleaned especially thoroughly at regular intervals.

Pressure is transmitted from button cap 5 to the probe 4 by an elastomer plunger 7 that tapers conically at its lower end and acts on the probe 4. The plunger 7 does not fill the cavity inside button cap 5 completely, so that button cap 5 tends to deform as it is inserted into housing 1.

With further reference to FIG. 3, the free space or cavity 11, within which the button cap 5 and projection 6 are located inside housing 1, is limited to a very small area around probe 4. Moreover, the acquisition structure 2 are potted inside the housing 1 by a potting compound 8 that avoids air inclusions trapped inside the housing 1 (e.g., eliminates air pockets between the cylinder 12 and the outer housing) while concomitantly holding the structure 2 inside the housing 1 so as to be generally resistant to vibration. In order to prevent penetration of the potting compound 8 into the space between tube 12 and inner tube 14, these tubes can be sealed at their anterior ends by a ring that seals off the above-mentioned intermediate space but has a central opening that allows the transmission means to extend into the inner tube 14.

The potting compound 8 can consist for example of a two-component silicone material that is thin when added to the housing 1 after the acquisition components 2 have been placed inside housing 1. By using removable fillers, the free space provided around probe 4 into which potting compound 8 does not penetrate, as shown in FIG. 3, can be kept clear as the compound sets. These fillers can be removed after the potting compound has set. Alternatively, this space can be kept clear with the aid of any suitable blocking tools, such as a cotton swab for example, with the potting compound 8 being kept at a distance from the probe 4 as it sets.

By omitting probe 4, the housing can be kept thinner as in FIG. 2 and can facilitate examinations in the mouth of a patient. Another source of relief for the patient is that two bends 16 spaced apart from one another are provided on the exploratory probe 9. In a preferred embodiment the bends extend in opposite directions. Thus sensor pin 10 can be guided relatively steeply behind the patient's teeth without the entire device having to be held at the same steep angle. The result is a smaller required aperture angle of the patient's mouth, so that first the treatment is more pleasant for the patient and second the risk of measurement errors caused by improper positioning of the sensor pin is reduced.

The functions to be triggered by the probe can also be provided in probe-less devices in which a foot switch is provided for example, with the transmission cable then being connected to the plug on a rear end 15 of the housing 1 and running first to the foot switch and from there to the computer.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A device for examining the gums of a patient, comprising
   an elongate housing having a connecting area for connecting a releasable, movable exploratory tip thereto,
   detection means coupled to the housing for detecting movement of the exploratory tip, said detection means being configured to be one of liquid-tight and liquid-resistant, and
   a potting compound disposed within said housing and surrounding at least partially said detection means.

2. Device according to claim 1, wherein said potting compound extends to an inside wall of said housing.

3. Device according to claim 1, wherein said detection means comprises at least one probe element having a probe cap coupled thereto, said probe cap extending through a wall of the housing and being operable from outside said housing.

4. Device according to claim 3, wherein said probe cap comprises a projection adapted for mounting within said housing.

5. Device according to claim 1, wherein said housing is free of externally projecting actuating elements and has a maximum outside diameter of about 1 cm adjacent the connecting area over a length of at least about 5 cm.

6. Device according to claim 1, wherein said exploratory tip comprises a wire or small tube having a plurality of bend portions formed therein, said bend portions being spaced apart along the length of the tip and being bent in opposite directions.

7. Device according to claim 1, further comprising means for transmitting data to evaluation and storage electronics.

8. Device according to claim 1, wherein said detection means comprises
   a circuit board mounted within said housing, and
   a probe element coupled to said circuit board.

9. Device according to claim 8, further comprising a plunger mounted within a first cavity formed within said housing, said plunger selectively engaging said probe.

10. Device according to claim 1, further comprising an endcap mounted to said housing and overlying one end of said plunger opposite said probe.

11. Device according to claim 1, wherein said detection means further comprises a first cylinder disposed within said housing, said cylinder being spaced from an interior wall of said housing to form a cavity therebetween, said potting compound being disposed within said cavity.

12. Device according to claim 11, further comprising a second cylinder mounted within said first cylinder and spaced from an interior wall of said first cylinder to form a second cavity, said second cavity being free of said potting compound.

13. Device according to claim 11, wherein said detection means further comprises a circuit board mounted within said housing, and a probe element coupled to said circuit board, said probe element being mounted within a second cavity in selective communication with said first cavity.

14. Device according to claim 13, wherein said second cavity is free of said potting compound.

15. Device according to claim 1, wherein said potting compound is formed of a plurality of parts.

16. Device according to claim 1, further comprising a replaceable cap mounted within an opening in said housing, said cap having a front portion that is exposed externally of the device and a bottom surface having a projection extending outwardly therefrom, said projection having a first flat surface and a second tapered surface extending away from said flat surface.

* * * * *